United States Patent [19]

McDaniel et al.

[11] Patent Number: 5,043,514

[45] Date of Patent: Aug. 27, 1991

[54] ETHYLENE DIMERIZATION AND POLYMERIZATION

[75] Inventors: Max P. McDaniel; Douglas D. Klendworth, both of Bartlesville, Okla.; Paul D. Smith, Seabrook, Tex.

[73] Assignee: Phillips Petroleum Company, Bartlesville, Okla.

[21] Appl. No.: 190,741

[22] Filed: May 5, 1988

Related U.S. Application Data

[63] Continuation of Ser. No. 822,453, Jan. 27, 1986, abandoned.

[51] Int. Cl.$^5$ ............................................. C07C 2/26
[52] U.S. Cl. ................................. 585/511; 526/97; 526/124; 526/129; 526/156; 585/522; 585/524
[58] Field of Search .................. 585/512, 522, 524; 526/97, 124, 129, 156

[56] References Cited

U.S. PATENT DOCUMENTS

| | | | |
|---|---|---|---|
| 4,076,929 | 2/1978 | Matsawa et al. | 526/97 |
| 4,284,748 | 8/1981 | Welch | 526/97 |
| 4,434,083 | 2/1984 | Van de Leemput et al. | 526/129 |
| 4,435,518 | 3/1984 | McDaniel et al. | 526/136 |
| 4,452,912 | 6/1984 | Bahadir et al. | 526/156 |
| 4,510,299 | 4/1985 | Lynch et al. | 526/124 |

FOREIGN PATENT DOCUMENTS

| | | | |
|---|---|---|---|
| 695451 | 10/1964 | Canada | 585/522 |
| 695215 | 9/1984 | Canada | 585/512 |
| 1182515 | 2/1970 | United Kingdom | 585/512 |

*Primary Examiner*—Asok Pal
*Attorney, Agent, or Firm*—Beverly M. Dollar

[57] ABSTRACT

A process for dimerizing ethylene comprising contacting ethylene with an insoluble solid catalyst and a cocatalyst, said catalyst having at least on the surface thereof hydrocarbyl ortho ester groups bonded to vanadium or titanium.

14 Claims, No Drawings

ETHYLENE DIMERIZATION AND POLYMERIZATION

This application is a continuation of application Ser. No. 822,453, filed Jan. 27, 1986, now abandoned.

FIELD OF THE INVENTION

The present invention relates to the conversion of ethylene to dimers, oligomers and higher polymers. In one aspect the present invention relates to a process specifically useful for the oligomerization of ethylene predominately to α-olefins.

BACKGROUND OF THE INVENTION

The catalysts generally employed for the oligomerization of ethylene are the result of the combination of Group VIII metal compounds and metal alkyl reducing agents. Examples are disclosed in U.S. Pat. No. 4,032,590.

There have been disclosures of the use of soluble complexes of transition metal esters and trialkyl aluminums as catalysts for the dimerization and oligomerization of ethylene. See for example, U.S. Pat. No. 2,943,125 and *Journal Of Polymer Science*, Vol. XXXIV, pp. 139–151 (1959).

Such transition metal based dimerization catalysts have even been proposed for use with polymerization catalysts to result in the in-situ dimerization of ethylene so that ethylene copolymers could be made without the employment of a separate comonomer stream. See U.S. Pat. No. 4,133,944 and *Journal Of Polymer Science*, Vol. XXII, pp. 3027–3042 (1984). These liquid transition metal catalyst compositions have been found to have a rapid drop-off in activity. In addition they have been found to tend to poison polymerization catalysts, thus limiting their usefulness in the cojoint dimerization and polymerization of ethylene.

SUMMARY OF THE INVENTION

One object of the present invention is to provide a dimerization process using a solid transition metal based catalyst having high activity and high selectivity to α-olefins.

Another object of the present invention is to provide a dimerization process having a more steady kinetic profile than provided prior art soluble transition metal catalysts.

Still another object of the present invention is to provide a transition metal dimerization process which does not tend to poison polymerization catalysts as do the prior art soluble catalysts.

Yet another object of the present invention is to provide a transition metal dimerization process which produces less gumming and fouling of the dimerization reactor than do prior art soluble transition metal catalysts.

In accordance with the present invention the dimerization of ethylene is achieved by using a catalyst consisting essentially of an insoluble solid having at least on the surface thereof hydrocarbyl ortho ester groups bonded to a transition metal in combination with an organometallic reducing agent.

DETAILED DESCRIPTION

The dimerization in accordance with this invention uses an insoluble solid having at least on the surface thereof hydrocarbyl ortho ester groups bonded to a transition metal selected from titanium and vanadium. The term hydrocarbyl ortho ester group is intended to denote groups of the formula -OR wherein R is a hydrocarbyl radical. Typically, R would have 1 to 10 carbon atoms.

Such materials which will remain solid during the dimerization can be formed by various means known in the art. One technique involves using a silica-titania cogel which has been treated with an alcohol, such as methanol to form bonds between the titanium and methoxy groups.

The currently preferred technique involves treating an inorganic porous solid particulate support with a hydrocarbyl ester of titanium or vanadium.

The supports used in making the dimerization catalyst in that manner are porous finely divided inorganic oxidic materials. Examples of typical oxidic materials include silica, alumina, silica-alumina, zirconia, thoria, magnesium oxide, aluminum phosphate and phosphated alumina. More specific examples include Davison 952 grade silica, aluminum phosphate, especially those having a phosphorus to aluminum ratio in the range of 0.6/1 to 0.9/1, and supports of the type disclosed in U.S. Pat. No. 4,364,841, the disclosure of which is incorporated herein by reference. Preferably the support has a high surface area and a large pore volume. The optimum particle size for the supports can be determined by routine experimentation. Typically, such supports have particle sizes in the range of about 200 microns to 0.1 micron. The internal porosity may be measured as the ratio between the pore volume and the weight of the support and can be determined by the BET-technique, described by S. Brunauer, P. Emmett, E. Teller in *Journal Of The American Chemical Society*, 60, pp. 209–319 (1938). Especially suitable are those supports having an internal porosity of at least about 0.6 cm$^3$/g. The surface area of the supports can be determined according to the above-mentioned BET technique, with the further use of the standardized method as described in *British Standards*, BS 4358. volume 1 (1969). Typically the surface area will be in the range of 100 to 600, more preferably 300 to 500 square meters per gram.

The support is generally calcined or otherwise treated with an oxygen-containing media such as air at an elevated temperature to dry and/or activate the support, as is common in the art, before the support is treated with the transition metal compound. As is known in the art activation temperatures vary depending upon the support selected. Aluminum phosphate supports are generally activated at a temperature in the range of 150° to 800° C., more commonly at a temperature in the range of 400° to 600° C. It has been noted that the higher activation temperatures sometimes result in a more active catalyst.

It is within the scope of the present invention to employ supports of the type described above which have been treated with organometallic reducing agents. Some of the preferred organometallic reducing agents are organomagnesium compounds of the formula MgR$_2$, wherein each R is independently selected from hydrocarbyl groups, most preferably alkyl groups, containing 1 to 30 carbon atoms; organoaluminum compounds of the formula AlR'$_3$, wherein each R' is selected from alkyl groups containing 1 to 12 carbon atoms; and mixtures thereof. Typical examples include triethylaluminum, tri-isobutyl aluminum, dibutyl magnesium, diethyl magnesium, dihexyl magnesium, dioctyl magnesium and organomagnesium-aluminum complexes of the general formula $(MgR_2)m\ (AlR'_3)n$, particularly those wherein the ratio of m/n is in the range of 2/1 to 10/1. Such organomagnesium aluminum complexes are disclosed in U.S. Pat. No. 4,004,071, the disclosure of which is incorporated herein by reference.

The treatment of the support with organometallic reducing agents is generally carried out by contacting the activated support with a solution of the reducing agent. Typical solvents include straight or branched saturated aliphatic hydrocarbons, such as butanes, pentanes, hexanes, heptanes, or commonly available mixtures such as gasoline, kerosene, gas oil, and the like. Cyclic hydrocarbons, like cyclopentane, cyclohexane, methylcyclohexane, and aromatic hydrocarbons such as benzene or chlorobenzene are also examples. From a practical point of view it is preferable to employ aliphatic hydrocarbons which are liquid at normal room temperatures but which can be readily removed by distillation.

Preferably when supports are produced using the organometallic reducing agents, the solution of the reducing agent and the support is heated to insure optimum bonding of the reducing agent to the support, typically this would be at temperatures in the range of 80° C. to 300° C., more generally about 100° C. to about 200° C. The pressure at which the treatment is carried out and the atmosphere employed is not particularly critical, but generally it would be carried out at about atmospheric pressure and in a non-oxidizing environment. The duration of the heat treatment necessary for obtaining optimum bonding at a given temperature can be determined by routine experimentation. Typically, it is sufficient to merely reflux the solution on the support for 10 minutes to an hour.

After the reaction between the support and the reducing agent has been completed the liquid and the solid are preferably separated before the support is contacted with the transition metal compound. This can be done by decanting, for example. It is generally desirable also to wash the solid several times with a solvent to remove reducing agent that is not bound to the support.

The quantities of reducing agent employed are not particularly critical. Obviously there is no advantage to using more reducing agent than can be bonded to the support since the unbonded material is preferably removed by the solvent when the dry solid is recovered.

The transition metal compounds employed in the present invention are non-halogenated compounds of titanium or vanadium containing three or more $OR''$ groups bonded to the metal wherein each $R''$ is individually selected from hydrocarbyl groups containing 1 to 10, more preferably 2 to 10 carbon atoms. Typically, it is preferred to employ compounds in which the $R''$ groups are alkyl or alkaryl. Some specific examples of such compounds include butyl titanate polymer, $Ti(OC_2H_5)_4$, $Ti(OC_3H_7)_4$, $Ti(OiC_3H_7)_4$, $Ti(OnC_4H_9)_4$, $Ti(OC_6H_4CH_3)_4$, $VO(OiC_3H_7)_3$, $VO(OC_2H_5)_3$, and $VO(OnC_4H_9)_3$. The most preferred transition metal compounds are those that are soluble in n-heptane at temperatures in the range of 50° to 70° C.

The treatment of the support with the transition metal is generally carried out by contacting the support with liquid containing the metal compound. It is generally preferred to use solutions of the transition metal compound.

Solvents employed can be of the same type as described above for use with reducing agents. The support is contacted with the transition metal compound under conditions conducive to the bonding of transition metal to the support. The temperature, pressure, and time employed for the contacting can vary over a wide range. Typically the temperature would be in the range of about 50° C. to about 300° C. more preferably in the range of about 50° C. to about 100° C. As a matter of convenience the contacting would generally be conducted at about atmospheric pressure. The duration of contacting necessary for obtaining optimum bonding at a given temperature can be determined by routine experimentation. Typically, it is sufficient to merely reflux the solution over the support for about 5 minutes to an hour.

After the reaction between the support and the transition metal compound, the liquid and the solid are separated. This can be done by evaporating or decanting. Generally it is preferable to wash the solid several times with a solvent to remove soluble transition metal remaining on the support.

If the resulting transition metal-containing support has not been subjected to temperatures of at least about 80° C. since the transition metal compound was added it is generally desirable to heat it for some time at a temperature of at least about 80° C. to about 200° C. to insure total activation of the catalyst before it is used in the dimerization.

The amount of transition metal added to the support can vary over a wide range. Generally, however, it is desirable to obtain as much bound transition metal as possible in the support, thus it is not unusual to produce catalysts containing 5 wt. % of the transition metal calculated on an elemental basis, more typically the catalyst will contain 2 to 4 weight percent of the transition metal.

When the catalyst is one which has been prepared using a support which has been treated with reducing agent as described above, it is generally desirable to prepare catalysts in which the molar ratio of the transition metal to the metal of the reducing agent, i.e., magnesium and/or aluminum, is at least about 1/1, more preferably greater than 1/1, most preferably 1 mole per reducing equivalent.

The solid dimerization catalyst is employed in conjunction with a cocatalyst comprising a trialkylaluminum reducing agent. The particularly preferred reducing agents are trialkylaluminum compounds of the type mentioned earlier.

The amount of cocatalyst employed can range over a fairly wide range, however the amount of cocatalyst employed can affect the catalyst activity. The amount of cocatalyst necessary for optimum activity will vary, depending upon the particular cocatalyst and dimerization catalysts employed. Typically, however the molar ratio of the metal of the reducing agent cocatalyst to the transition metal of the solid dimerization catalyst will be in the range of about 5/1 to 1/5, more preferably about 2/1 to 1/1.

The reaction conditions for the dimerization can also vary over a wide range. The reaction is effected by merely contacting ethylene with the mixture of the catalyst and cocatalyst. The ethylene pressure typically would be in the range of about 0.2 to 20 atmospheres, more preferably about 1 to 10 atmospheres. It is within the scope of the invention to have hydrogen present during the reaction. In fact in many cases the employment of hydrogen results in increased activity. When employed the hydrogen pressure would generally be in the range of about 1 to 6 atmosphere.

The temperature at which the reaction is begun can also vary over a wide range, typically in the range of about 20° C. to about 150° C., though temperatures in the range of 30° C. and 100° C. would be more common, with tempertures in the range of about 50° to 100° C. being generally most preferred.

In an especially preferred embodiment of the present invention the solid dimerization catalyst is used in conjunction with an ethylene polymerization catalyst so that ethylene copolymers can be produced directly from ethylene.

The polymerization catalyst empoyled can be a solid transition metal polymerization catalyst. Many such catalysts are known in the art and are available commercially. Typically the catalysts are based on the transition metals titanium, zirconium, or vanadium. Some typical examples of such catalysts include the Stauffer-type $TiCl_3.0.33AlCl_3$ and titanium, magnesium-containing catalysts such as disclosed in U.S. Pat. Nos. 4,198,718; 4,069,169; 4,347,158; 4,325,837; 4,326,988; 4,400,303; 4,394,291; 4,391,736; 4,363,746 and 4,312,784, the disclosures of which are incorporated herein by reference. The cojoint dimerization/polymerization is conducted using the same types of reaction condition normally employed with the polymerization catalysts, including the use of the cocatalysts generally used with those catalysts. Generally the preferred cocatalysts are trialkylaluminum compound in which the alkyl groups contain no more than about four carbon atoms. Since it has been noted that organoaluminum halides generally have an adverse effect on the activity of the dimerization catalyst it is generally preferable to use polymerization catalyst/cocatalyst combinations that are free of significant amounts of soluble organoaluminum halides. Examples of particularly useful cocatalysts include triethylaluminum and trimethylaluminum.

Since the amount of cocatalyst employed can affect the activity of the dimerization catalyst, the amount of cocatalyst employed with the polymerization catalyst will vary depending upon the results desired.

Further, it is noted that as the ratio of the dimerization catalyst to polymerization catalyst increases the density of the polymer generally decreases which indicates that larger amounts of dimerization are occurring. Accordingly the ratio of the dimerization catalyst to the polymerization catalyst can be varied depending on the results desired.

A further understanding of the present invention and its advantages will be provided by a review of the following examples.

EXAMPLE I

Dimerization in Liquid Catalyst

A liquid catalyst was prepared by adding 3.0 ml of $Ti(OC_2H_5)_4$ to 100 ml of toluene and then adding 5.33 ml of a 15 weight percent solution of triethylaluminum. An emerald green solution resulted. To carry out the dimerization 16 ml of the emerald green solution was added to an autoclave along with 1.0 ml of the 15 weight percent triethyl aluminum solution and one liter of isobutane at 80° C. Ethylene was then supplied on demand at 550 psig. Only a weak reaction of the ethylene was observed. After 20 minutes another 1 ml of the TEA solution was added and the rate soared to 578 gms/hr. Within 10 minutes later it had dropped to 348 gm/hr. Nine minutes later another ml of the TEA solution was added, and the rate picked up to 848 gm/hr but soon began dropping again and was 448 gm/hr by the time 1 hr had passed since the dimerization reaction had first begun. The reactor when opened was found to contain a scum of polymer.

A second experiment was carried out in the same manner except that this time even more TEA was added to explore further the effect of the TEA. The results can be summarized as follows:

| TEA/Ti Ratio | 0.5 | 1.0 | 1.6 | 2.0 | 2.9 |
|---|---|---|---|---|---|
| Initial Consumption | 0 | 578 | 848 | 1008 | 0 |

From this it was concluded that if the amount of TEA was too high it had an adverse effect on the activity. It was also noted that the activity always dropped quickly after the addition of the TEA, regardless of the TEA/Ti ratio. The activity of the total runs in terms of grams of ethylene consumed per gram of titanium for the two one hour reactions were calculated to be 2975 g/g Ti-hr and 2025 g/g Ti-hr, respectively. It should be noted however, that since the activity drops quickly with time these catalysts had very little activity shortly after each TEA addition. Accordingly, these values are unrealistically high if one is concerned with a steady reaction rate.

EXAMPLE II

Dimerization in Liquid Catalyst

In this run 2.0 ml of $Ti(OEt)_4$ was added to 24.6 g of toluene and then 11.5 mls of magala (a solution of 7 moles ethyl-butyl magnesium and 1 mole trialkylaluminum) was added with slow stirring. This was a Mg/Ti molar ratio of 0.5/1. The solution turned blue-green. After setting overnight a fine blue-green precipitate formed. Before that, however, 16 ml of the blue-green solution was added to the reactor as in Example 1 with 1 ml of the TEA solution. Upon supplying ethylene there was an active consumption of ethylene but within about 10 minutes the activity was only about half that of the initial activity. Another ml of TEA was added, but only a minor improvement in activity resulted. After 48 minutes, the reaction was shut down, since the activity had dropped to only 19% of its initial value. The activity on an hourly basis for this run was calculated as 1265 g/g Ti-hr.

A duplicate of the above experiment was conducted. It gave an activity of 1900 g/g Ti-hr. Again it was noted that there was a severe loss in activity within about 10 minutes after the TEA was added.

EXAMPLE III

Solid Catalyst A Preparation

An aluminophosphate having a phosphorus-/aluminum ratio of about 0.9 was calcined in air for 3 hours at 600° C. Then 7.3 gm of the calcined support was slurried in about 30 ml of heptane, to which 16.8 ml of magala solution was added. This was calculated to be an amount of magnesium equal to about 5% of the support weight. The slurry was refluxed for ten minutes, then the excess liquid was drained off, and the solid rinsed in heptane twice to remove remaining soluble magnesium. Then 7.7 ml of titanium tetraethoxide was added to the support. This was calculated as being about 2.5 moles of Ti per mole of Mg. This resulted in a blue-green solid and a blue solution. The slurry was refluxed five minutes, the liquid was then drained off and the solid was washed several times with isopentane.

The solid was then dried under flowing nitrogen on a hot plate at 50°–100° C.

EXAMPLE IV

Dimerization with Solid Catalyst A

Exactly 0.9111 gm of Catalyst A was introduced into a 2 liter autoclave along with 1.0 ml of a 15 weight percent solution of triethyl aluminum and one liter of isobutane 80° C. Ethylene was then supplied on demand at 550 psig. Immediately a large heat of reaction was noticed and a consumption of ethylene of at least 600 g/hr was observed. The activity was high and substantially constant throughout the reaction which was stopped 30 minutes later. Integration of the flow rate indicated that at least 225 gm of ethylene had been consumed. This gives an activity in terms of grams of ethylene consumed per gram of titanium per hour of 12,350! When the reactor door was opened, no polymer was found, only a liquid having a strong olefinic odor.

Another dimerization reaction was carried out with Catalyst A using a smaller Ti/TEA ratio. In this case 0.7701 gms of the solid catalyst was used with 2.0 ml of the TEA solution. Again a strong reaction was obtained which remained strong over the 30 minute reaction period. The activity was calculated as 12,500 grams of ethylene/gram Ti-hr. The reactor was found to contain about 6 gms of polymer. The solution in the reactor was analyzed by GLC and the results were as follows:

| 1-butene | 96.5 mole % |
|---|---|
| 2-butene | trace |
| hexenes | 2.9 mole % |
| heptenes | 0.3 mole % |
| octenes | 0.2 mole % |

Thus the reaction was highly selective to the production of 1-butene.

Another dimerization reaction was conducted with Catalyst A, this time employing hydrogen. Exactly 0.7228 gm of A was added along with 1 mL of the TEA solution and 100 psi of hydrogen. The ethylene was supplied at 450 psi. This time an even stronger reaction was obtained, giving a steady flow rate of over 700 gm/hr. The integral indicated that 308 grams of ethylene had been consumed in 26 minutes, giving an activity of 24,700 gms of ethylene/gm Ti-hr. Only a trace of polymer was found.

The solution in the reactor was analyzed by GLC and the results were as follows:

| 1-butene | 87.2 mole % |
|---|---|
| cis-2-butene | 0.6 mole % |
| trans-2-butene | 1.4 mole % |
| hexenes and higher | 10.7 mole % |

The hydrogen thus improved the activity of the catalyst without changing its selectivity to 1-butene very much.

EXAMPLE V

A solid was prepared in the same manner as described in Example III except that in the last step the isopentane wash liquid was merely evaporated at room temperature rather than having the solid heated at 50° to 100° C. on a hot plate under flowing nitrogen. This gave a blue-purple solid which did not catalyze a reaction with ethylene.

EXAMPLE VI

The solid of Example V was heated in nitrogen at 100° C. for a few minutes and it turned green. This green solid will be referred to as Catalyst B. In a dimerization run 0.7393 gm of Catalyst B gave a flow of over 400 gm of ethylene/hr. This calculated as an activity of 12,350 gms of ethylene/gm of Ti-hr. The activity was almost constant over the whole 30-minute reaction time.

EXAMPLE VII

Silica as Support

Solid catalysts were prepared using Davison 952 grade silica as the support. The support was calcined at 400° C. in air.

In one case 8.0 gms of the calcined silica was slurried in a hydrocarbon and 8 mols of the magala solution was added. The slurry was refluxed, the excess liquid drained off and the solid rinsed with hydrocarbon. The solid was then contacted with 3.2 ml of titanium tetraethoxide at 80° C. The solid was then washed with hydrocarbon and dried over low heat in a nitrogen stream to give Catalyst C.

A Catalyst D was prepared in a similar manner using 9.3 gms of the calcined silica, 9.3 ml of the magala solution, and 1.5 ml of the titanium tetraethoxide.

Catalyst C and D were tested in a 2-liter bench reactor under particle form conditions using a TEA cocatalyst and 50 psig hydrogen. Catalyst C gave an activity of 14,750 gms of ethylene per gram of Ti-hr. Catalyst D gave an activity of 16,750 gms of ethylene per gram of Ti-hr. Only minor amounts of polymer were obtained. GLC of the non-polymeric products showed the catalysts to be highly selective to 1-butene. Greater than 98 mole percent of the liquid was 1-butene.

EXAMPLE VIII

Catalyst Prepared Without Reductant

Catalysts were prepared by contacting calcined Davidson 952 grade silica with Ti(OEt)$_4$ at 80° C., washing off the excess titanium and then drying over low heat in a nitrogen stream.

Catalyst E was prepared using 7.0 gm of the silica and 7 ml of Ti(OEt)$_4$.

Catalyst F was prepared using 5.4 gm of the silica and 5.4 gm of the Ti(OEt)$_4$.

When employed in contact with TEA on ethylene both catalysts gave high activities which dropped off much less rapidly with time than did the liquid catalysts. Both gave only minor amounts of polymer. Catalyst E gave an activity of 15,900 gms of ethylene/gm Ti-hr and Catalyst F 13,350 gm/Ti-hr.

EXAMPLE IX

Cojoint Dimerization/Polymerization With Liquid Catalyst

Tests were made to evaluate suggestions made in the literature about using the liquid catalysts of Example 1 in conjunction with a polymerization catalyst to cause the cojoint dimerization and polymerization of ethylene to give ethylene copolymers.

The polymerization catalyst employed was a commercial catalyst of the type sold by Catalyst Resources, Inc. under the trade name Lynx 705. That catalyst is one of the type disclosed in U.S. Pat. No. 4,347,158, the disclosure of which is incorporated herein by reference.

The Lynx 705 catalyst when used in the amount of 0.0489 gm along with 1 ml of TEA gave 4622 gm of polymer in 26 minutes. There was no evidence of olefin production.

To carry out a cojoint polymerization/dimerization 0.0691 gm of Lynx 705 catalyst and 8 ml of the blue-green solution of Example 10 were added along with 2 ml of TEA to the reactor. Ethylene consumption started at 336 gm/hr but dropped quickly to 73 gm/hr in 20 minutes. Only a scum of polymer was found in the reactor.

In another run 0.1289 gm of the Lynx 705 catalyst and 1 ml of TEA were employed and 0.5 ml of Ti(OEt)$_4$ was employed in place of the blue-green solution. There was no evidence of either polymerization or dimerization. This shows that the soluble Ti(OEt)$_4$ tends to poison the polymerization catalyst. A similar observation is reported in *Journal Of Polymer Science, Polymer Chemistry Edition*, Vol. 22, pp. 3034 and 3037.

EXAMPLE 10

Cojoint Dimerization/Polymerization With Solid Catalyst

A solid dimerization catalyst was made by reacting 10.5 gm of Davison 952 grade silica calcined at 400° C. with 10.5 ml of Ti(OEt)$_4$ in heptane slurry and then rinsing off the excess Ti with three heptane washes. This catalyst in the amount of 0.4521 gm, was charged to the reactor along with 0.0621 gm of Lynx 705 catalyst and 1 ml of TEA. A vigorous reaction started and grew rapidly until by 10 minutes the reaction had to be shut down because it could not be controlled, due to overheating. When the reactor was opened, 45 gm of polymer was recovered which smelled strongly of butene. Calculated productivity was 725 g/gm in 10 minutes which is close to that obtained in a control run in which 0.0357 gm of the Lynx 705 catalyst was used with 1 ml of TEA in the absence of dimerization catalyst.

Since it is known that copolymerization generally never occurs as easily as homopolymerization it thus follows that the solid dimerization catalyst did not give any evidence of poisoning the polymerization catalyst.

EXAMPLE II

Solid Vanadium Catalyst

A catalyst was prepared by dissolving 3.0 gms of VO(OiPr)$_3$ in 30 ml of anhydrous heptane. The solution was mixed with 11.40 grams of Davison 952 grade silica which had been calcined at 400° C. The solid and the liquid were separated and the solid dried as in the previous preps by heating on a hot plate under a stream of nitrogen.

In one experiment 2.0821 gms of the solid catalyst was added to the reactor with 1 ml of the TEA solution. In 30 minutes 39 grams of product was made, of which 36 grams were polymer. A strong odor of butene and hexene was detected in the reactor and on the polymeric product. The conditions were 100° C., 550 psi ethylene and 1 liter of isobutane.

In another experiment the catalyst was used in combination with hydrogen. In this case 65 grams of product was produced in 30 minutes, of which 43 grams was polymer. Again a strong odor of butene and hexene was detected in the reactor and on the polymeric product.

That which is claimed:

1. A process for the dimerization of ethylene consisting essentially of: (a) contacting ethylene under suitable reaction conditions with a halogen free dimerization catalyst prepared by contacting activated finely divided inorganic oxidic support with a non-halogenated transition metal compound of titanium selected from the group consisting of butyl titanate polymer, Ti(OC$_2$H$_5$)$_4$, Ti(OC$_3$H$_7$)$_4$, Ti(OiC$_3$H$_7$)$_4$, Ti(OnC$_3$H$_9$)$_4$, and Ti(OC$_6$H$_4$CH$_3$)$_4$, under conditions sufficient to bond the transition metal to the support, drying, and activating the resulting solid, and a cocatalyst comprising an organometallic reducing agent, said solid catalyst consisting essentially of an insoluble solid having at least on the surface thereof hydrocarbyl ortho ester groups bonded to titanium wherein the molar ratio of said cocatalyst to titanium is in the range of 5:1 to 1:5; and (b) recovering the thus dimerized ethylene.

2. A process according to claim 1 wherein said support has been treated with organometallic reducing agent prior to contact with said transition metal compound, wherein said reducing agent is selected from compounds of the formula MgR$_2$ and AlR'$_3$, where each R is independently selected from hydrocarbyl groups containing 1 to 30 carbon atoms and each R' is independently selected from alkyl groups containing 1 to 12 carbon atoms.

3. A process according to claim 1 wherein said support is selected from the group consisting of silica, alumina, silica-alumina, zirconia, thoria, magnesium oxide, aluminum phosphate and phosphated alumina.

4. A process according to claim 1 wherein said transition metal compound is a butyl titanate polymer.

5. A process according to claim 1 wherein said transition metal compound is Ti(OC$_2$H$_5$)$_4$.

6. A process according to claim 1 wherein said cocatalyst is selected from trialkylaluminum compounds.

7. A process according to claim 6 wherein said cocatalyst comprises triethylaluminum.

8. A process according to claim 7 wherein the molar ratio of said triethylaluminum cocatalyst to titanium atoms in said catalyst is in the range of 2:1 to 1:1.

9. A process according to claim 7 wherein said transition metal compound is Ti(OC$_2$H$_5$)$_4$.

10. A process according to claim 8 wherein said support is aluminum phosphate.

11. A process according to claim 8 wherein said support is silica.

12. A process according to claim 8 wherein said support has been treated with ethyl butyl magnesium.

13. A process for the dimerization of ethylene comprising contacting ethylene under suitable reaction conditions with
   an insoluble solid dimerization catalyst prepared by contacting an activated finely divided inorganic support selected from silica and aluminum phosphate with Ti(OC$_2$H$_5$)$_4$, wherein said support has been treated with ethyl butyl magnesium and triethylaluminum and wherein said solid catalyst is thereafter dried and activated; and
   a cocatalyst consisting essentially of triethylaluminum, wherein the molar ratio of said triethylaluminum cocatalyst to titanium atoms in said catalyst is in the range of 2:1 to 1:1; and recovering the thus dimerized ethylene.

14. A process for the dimerization of ethylene comprising contacting ethylene under suitable reaction conditions with an insoluble solid dimerization catalyst prepared by contacting an activated finely divided inorganic oxidic support with butyl titanate polymer and drying and activating the resulting solid; and a cocatalyst comprising an organometallic reducing agent; and recovering the thus dimerized ethylene.

* * * * *